United States Patent [19]

Stanley et al.

[11] Patent Number: 5,291,887

[45] Date of Patent: * Mar. 8, 1994

[54] APPARATUS AND METHODS FOR NONINVASIVE BLOOD SUBSTANCE MONITORING

[75] Inventor: Theodore H. Stanley, Salt Lake City; Jie Zhang, West Valley City, both of Utah

[73] Assignee: Anesta Corporation, Salt Lake City, Utah

[*] Notice: The portion of the term of this patent subsequent to Aug. 18, 2009 has been disclaimed.

[21] Appl. No.: 892,287

[22] Filed: Jun. 2, 1992

Related U.S. Application Data

[63] Continuation-in-part of Ser. No. 360,876, Jun. 2, 1989, Pat. No. 5,139,023.

[51] Int. Cl.$^5$ .................................................. A61B 5/00
[52] U.S. Cl. ......................................... 128/637; 128/760; 128/898; 128/632; 604/289; 514/975
[58] Field of Search .......................... 128/637, 760, 767; 604/19, 20, 892.1, 891.1, 890.1, 304, 307; 514/975

[56] References Cited

U.S. PATENT DOCUMENTS 2,561,071 7/1951 Prisk ..................................... 128/260
3,053,255 9/1962 Meyer ................................... 128/260
3,289,671 12/1966 Troutman et al. .................... 128/2.1

(List continued on next page.)

FOREIGN PATENT DOCUMENTS

WO86/00536 1/1986 PCT Int'l Appl. .
WO90/02511 9/1988 PCT Int'l Appl. .

OTHER PUBLICATIONS

Aungst, Brude J. et al., "Comparison of Nasal, Rectal, Buccal, Sublingual and Intramuscular Insulin Efficacy and the Effects of a Bile Salt Absorption Promoter," The Journal of Pharmacology and Experimental Therapeutics, vol. 244, No. 1, pp. 23-27 (1988).

Banag, Ajay K. et al., "Systemic Delivery of Therapeu- (List continued on next page.)

Primary Examiner—C. Fred Rosenbaum
Assistant Examiner—Chalin Smith
Attorney, Agent, or Firm—Workman, Nydegger & Jensen

[57] ABSTRACT

The present invention is directed to novel methods and apparatus for noninvasively collecting substances through mucosal tissues. The concentration of a substance in blood is monitored noninvasively by correlation with the amount of the substance which permeates a mucosal membrane into a substance receiving medium over a specified time period. The substance receiving medium may include an substance permeation enhancer capable of increasing the substance permeability across the mucosal membrane. The substance receiving medium is positioned against the mucosal membrane. After sufficient time delay, the substance receiving medium is removed and analyzed for the concentration of a substance to be measured using known analytical techniques.

The apparatus within the scope of the present invention includes means for supporting the substance receiving medium. The means for supporting the receiving medium provides an added benefit of isolating the substance receiving medium from contamination sources. Such means for supporting the substance receiving medium may include a housing defining a receiving chamber therein which holds the substance receiving medium and an opening to the receiving chamber. The apparatus also preferably includes means for temporarily positioning the substance receiving medium against the mucosal membrane.

The present invention also naturally utilizes the mucosa as filter membrane to exclude compounds in plasma that would interfere with any analysis or make any analysis more difficult. Analysis of substances in receiving medium may be significantly easier than in plasma. An artificial membrane may be used to further exclude other undesirable compounds.

58 Claims, 5 Drawing Sheets

U.S. PATENT DOCUMENTS

| | | | |
|---|---|---|---|
| 3,323,774 | 6/1967 | Wilson | 251/125 |
| 3,794,910 | 2/1974 | Ninke et al. | 324/30 R |
| 4,014,334 | 3/1977 | Theeuwes et al. | 128/760 |
| 4,071,020 | 1/1978 | Pugliese | 128/2 |
| 4,116,241 | 9/1978 | Theeuwes et al. | 128/260 |
| 4,151,832 | 5/1979 | Hamer | 128/765 |
| 4,190,060 | 2/1980 | Greenleaf et al. | 128/760 |
| 4,200,110 | 4/1990 | Peterson et al. | 128/634 |
| 4,220,158 | 9/1980 | Delpy et al. | 128/632 |
| 4,250,163 | 2/1987 | Nagai et al. | 424/14 |
| 4,292,299 | 9/1981 | Suzuki et al. | 424/16 |
| 4,321,252 | 3/1981 | Keith et al. | 424/28 |
| 4,325,367 | 4/1982 | Tapper | 128/207.21 |
| 4,364,385 | 12/1982 | Lossef | 128/213 R |
| 4,379,454 | 4/1983 | Campbell et al. | 604/897 |
| 4,398,543 | 8/1983 | Sandlin et al. | 128/760 |
| 4,401,122 | 8/1983 | Clark, Jr. | 128/635 |
| 4,457,748 | 7/1984 | Lattin et al. | 604/20 |
| 4,458,686 | 7/1984 | Clark, Jr. | 128/635 |
| 4,460,370 | 7/1984 | Allison et al. | 604/897 |
| 4,538,616 | 9/1985 | Rogoff | 128/632 |
| 4,542,750 | 9/1985 | Ettare | 128/760 |
| 4,542,751 | 9/1985 | Webster et al. | 128/760 |
| 4,548,922 | 10/1985 | Carey et al. | 514/4 |
| 4,557,723 | 12/1985 | Sibalis | 604/20 |
| 4,573,996 | 3/1986 | Kwiatek et al. | 604/897 |
| 4,588,580 | 5/1986 | Gale et al. | 424/21 |
| 4,594,326 | 6/1986 | Wade | 436/501 |
| 4,622,031 | 11/1986 | Sibalis | 604/20 |
| 4,635,488 | 1/1987 | Kremer | 73/864.72 |
| 4,640,689 | 2/1987 | Sibalis | 604/30 |
| 4,671,953 | 6/1987 | Stanley et al. | 424/440 |
| 4,690,683 | 9/1987 | Chien et al. | 604/896 |
| 4,693,711 | 9/1987 | Bremer et al. | 604/306 |
| 4,706,676 | 11/1987 | Peck | 128/632 |
| 4,710,191 | 12/1987 | Kwiatek et al. | 604/897 |
| 4,723,958 | 2/1988 | Pope et al. | 604/890 |
| 4,743,249 | 5/1988 | Loveland | 424/447 |
| 4,746,508 | 5/1988 | Carey et al. | 424/88 |
| 4,747,841 | 5/1988 | Kuratomi et al. | 604/291 |
| 4,819,645 | 4/1989 | Peck | 128/632 |
| 4,821,733 | 4/1989 | Peck | 128/632 |
| 4,846,182 | 7/1989 | Fogt et al. | 128/632 |
| 4,889,721 | 12/1989 | Ueda et al. | 424/448 |
| 4,892,737 | 1/1990 | Bodor et al. | 424/449 |
| 4,904,475 | 2/1990 | Gale et al. | 424/449 |
| 4,909,256 | 3/1990 | Peck | 128/632 |
| 4,957,108 | 9/1990 | Schwendorfer et al. | 128/632 |
| 4,960,467 | 10/1990 | Peck | 128/632 |
| 5,056,521 | 10/1991 | Parsons et al. | 128/898 |
| 5,113,860 | 5/1992 | McQuinn | 128/632 |
| 5,139,023 | 8/1992 | Stanky et al. | 128/637 |

OTHER PUBLICATIONS tic Peptides and Proteins," International Journal of Pharmaceutics 48, pp. 15–50 (1988).

Ishida, Masami, "New Muycosal Dosage Form of Insulin," Chemica Pharmaceutical Bulletin, vol. 29, pp. 810–816 (1982).

Machol, Libby, "Innovative Ways to Administer Drugs," Technology (1989), pp. 85–103.

Micossi, P. et al., "Free-Insulin Profiles After Intraperitoneal, Intramuscular and Subcutaneous Insulin Administration," Diabetes Care, vol. 9, No. 6, pp. 575–578 (Nov.–Dec. 1986).

Mishima, Motchiro et al., "Studies on the Promoting Effects of Mediuym Chain Fatty Acid Salts on the Nasal Absorption of Insulin in Rats," Journal of Pharmacobiodynamics. Col. 10, pp. 624–631 (1987).

Robinson, Joseph R., "Mucoadhesive Drug Delivery Systems: Buccal Drug Delivery, Potential Close to Fruition?" Welcome Trends in Hospital Pharmacy, pp. 8–12 (Jan. 1989).

"Conrex Pharmaceutical Advances Drug Delivery Methods."

APPARATUS AND METHODS FOR NONINVASIVE BLOOD SUBSTANCE MONITORING

RELATED APPLICATIONS

This patent application is a continuation-in-part of co-pending patent application Ser. No. 07/360,876, filed Jun. 2, 1989, now U.S. Pat. No. 5,139,023 in the names of Theodore H. Stanley, Charles Dewey Ebert, Jie Zhang and William I. Higuchi and entitled "APPARATUS AND METHODS FOR NONINVASIVE BLOOD GLUCOSE MONITORING," which is incorporated herein by specific reference.

BACKGROUND

1. The Field of the Invention

The present invention is directed to methods and apparatus for monitoring the concentrations of certain substances in the blood of an individual. More particularly, the concentrations of natural and synthetic substances, present in an individual's body or introduced from an external source, are monitored noninvasively through diffusion across epithelial membranes, preferably the mucosal epithelial tissues within the mouth.

2. Technology Review

The blood is routinely tested for various blood constituents in countless medical procedures. This generally involves drawing an actual blood sample from the individual, followed by blood analysis. Typically, blood testing is a prophylactic or subsequent response to some type of disease.

The different types of substances which are routinely tested are quite diverse. One classification of the type of substances which are routinely tested are substances that naturally occur in a human body. This can include protein substances such as amino acids, and carbohydrate substances such as glucose.

Another classification of the type of substances which are routinely tested are substances which are introduced into a human body from an external source. These types of substances may be produced naturally or synthetically. Often, these types of drugs require dose-to-effect monitoring because of their toxic nature and to ensure therapeutic effectiveness. Examples of some types of externally derived substances include but are not limited to alcohol, narcotics, bronchodilators, diuretics, asthmatics, substances of abuse, and intravenous anesthetics.

The most accurate method of determining the presence of a substance in a subject's blood is to actually draw a blood sample and analytically measure it for the presence of the substance. Unfortunately, most individuals dislike giving blood samples. In addition, extraction of blood carries the risk of transmitting diseases, such as AIDS. There are also legal issues which arise from invasively drawing blood against the subject's will. Hence, there is a need for devices and methods for noninvasively measuring the presence of a substance in an individual's blood.

Attempts have been made to monitor the level of a substance in an individual's blood noninvasively. As used in this specification, the term "noninvasive blood substance monitoring" means determining the concentration of a substance in an individual's blood without actually drawing the blood. These attempts to monitor the level of a substance in blood noninvasively have most often taken the form of monitoring an individual's saliva or breath.

Measurement of the content of a substance in an individual's blood by a breathalyzer test may be inaccurate because the proportion of a substance in a person's breath is not always proportional to the amount of the substance in a person's blood stream. For example, a person having consumed an alcoholic beverage within a certain time period (i.e. 15 minutes) will register a higher alcohol content on a breathalyzer device than a simultaneously tested blood monitoring device. A certain amount of time must elapse before alcohol in an individual's expiration will correlate with alcohol in an individual's blood stream.

Likewise, efforts to monitor the level of a substance in the blood of an individual based upon the concentration of the substance in an individual's saliva can prove unsatisfactory. It is possible that saliva can become diluted, more concentrated or otherwise contaminated prior to any testing to monitor the concentration of the substance. The imprecise result of any such factors would thereby yield incorrect results.

Therefore, efforts to monitor the concentration of a substance in the blood of an individual based upon the concentration of the substance in an individual's saliva or breath are avoided because both saliva and breath are subject to factors which can lead to incorrect concentrations of the substance level in a person's blood.

There has also been an attempt in the prior art to monitor the concentration of a substance in the blood of an individual noninvasively by treating dermal layers with enzymes which react with the substance. The concentrations of the substance in the epidermal layers can then be determined by monitoring the enzyme reactions. However, these procedures cannot be considered noninvasive because compounds are introduced into the person's epidermal layers. Additionally, the compounds are allowed to react within the person's body, subjecting the dermal environment to reaction by-products.

In view of the foregoing, it will be appreciated that it would be a significant advancement in the art to develop an apparatus and methods for noninvasively monitoring the presence of a substance in the blood.

It would be another significant advancement in the art to provide apparatus and methods for noninvasively monitoring the concentration of a substance in the blood which accurately and reproducibly correlate with actual concentrations of the substance in the blood.

Also, it would be another significant advancement in the art to provide apparatus and methods for noninvasively monitoring the concentration of a substance in the blood without the possibility of contamination which can produce inaccurate reporting of the actual concentration of the substance in the blood.

Additionally, it would be a significant advancement in the art to provide apparatus and methods for noninvasively monitoring the concentration of a substance in the blood which can be performed rapidly.

It would be yet another significant advancement in the art to provide apparatus and methods for noninvasively monitoring the concentration of a substance in the blood which are not limited to certain individuals, but instead can be applied to a wide variety of individuals.

It would further be a significant advancement in the art to provide apparatus and methods for noninvasively monitoring the concentration of a substance in the blood which can be performed at a location, and at a point in time, where and when an individual is first required to be monitored for the concentration of the substance.

Such apparatus and methods for noninvasively monitoring the concentration of a substance in blood are disclosed and claimed herein.

BRIEF SUMMARY AND OBJECTS OF THE INVENTION

The present invention is directed to novel methods and apparatus for noninvasive blood substance monitoring. According to the present invention, the concentration of substances in the blood is monitored noninvasively by collecting substances which passively diffuse across mucosal membranes and then measuring the concentration of the substances correlating the sample concentration with the actual blood concentration.

It is preferred, in accordance with the invention, to monitor blood substances noninvasively by collecting substances that passively diffuse across mucosal epithelial membranes. Mucosal membranes are generally permeable to many substances. Examples of mucosal membranes include buccal, nasal, rectal and gastrointestinal. Therefore, the substances will diffuse across the mucosal membranes into the monitoring device of the present invention.

Dermal membranes, although similar to mucosal membranes in that they are permeable to some substances, are generally not preferred to monitor substances noninvasively because the dermal membranes have a much lower permeability coefficient, and therefore a much longer lag time than mucosal membranes. For most substances, although not all substances (i.e. alcohol), dermal membranes require an additional step to be taken in order to monitor blood substances in the present invention. Generally, such an additional step comprises the application of a permeation enhancer to the dermal membranes. A permeation enhancer improves the substance permeability across an epithelial membrane.

In one preferred embodiment within the scope of the present invention, a substance diffuses across a mucosal membrane, such as the buccal membranes, into a substance receiving medium. The substance receiving medium is positioned against the mucosal membrane, and after a predetermined time period, the substance receiving medium is removed and analyzed for the concentration of the substance using conventional analytical techniques.

Since the substance receiving medium can be positioned against the mucosal membrane and the substance diffuses directly into the medium, contamination of the medium and mucosal sample are greatly reduced. By isolating the substance receiving medium from saliva and other fluids which may be present in an individual's mouth, inaccurate results from contamination are eliminated.

The substance concentration gradient across the mucosal tissue provides the driving force for diffusion from the blood into the substance receiving medium. The substance receiving medium preferably maintains a much lower concentration of the substance being measured for the entire duration of the measurement ("sink condition"); while the submucosal interstitial fluid, which is in equilibrium with the blood perfusing the mucosal membranes, has a substantially higher substance concentration. Under these conditions, a straight line correlation between the concentration of the substance diffusing into the substance receiving medium per unit time, and the concentration of the substance in an individual's blood stream has been found.

The apparatus within the scope of the present invention includes means for supporting and isolating the substance-receiving medium. Such means for supporting and isolating the substance receiving medium may include a housing which holds and contains the substance receiving medium. The housing functions to isolate the substance receiving medium from substance contamination sources by providing an impenetrable barrier about substantially all of the substance receiving medium.

The apparatus also includes means for joining the substance receiving medium to the mucosal membrane. For example, if the apparatus includes a housing for supporting and isolating the substance receiving medium, then an adhesive composition is preferably used to join the substance receiving medium to the mucosal membrane.

The joining means may also include a hydrogel or other support materials which perform substantially the same function as a hydrogel. If the apparatus includes a hydrogel for supporting the substance-receiving medium, then the hydrogel itself adheres directly to the mucosal membrane. Such other support materials include liquids, creams, emulsions, suspensions, and other solid and semisolid media.

In addition, the apparatus includes means for temporarily positioning the substance receiving medium against the mucosal membrane may include a configuration wherein a stick or holder aids in properly positioning the device against the mucosal membrane. Also, the means for temporarily positioning the substance receiving medium against the mucosal membrane may include a clamping device on the housing which presses and holds the substance receiving medium against the mucosal membrane.

An important feature of the present invention is that the invention utilizes the diffusion rate limiting properties of the mucosal tissues. It will be appreciated that the overall rate that a substance diffuses through the mucosal membrane into the substance receiving medium depends upon the individual substance permeabilities of the membranes that the substance must pass through to enter the substance receiving medium. The overall substance diffusion rate is determined by the net resistance of all diffusional components, the net diffusion being dominated by the single diffusion component with the lowest substance permeability. Thus, the use of mucosal tissues provides precise and reproducible permeability, and the overall substance diffusion rate may be maintained relatively constant.

The present invention may also utilize the diffusion rate limiting properties of an artificial semipermeable membrane. As above, the overall rate that a substance diffuses through the artificial membrane into the substance receiving medium depends upon the individual substance permeabilities of the membranes that the substance must pass through to enter the substance receiving medium. The overall substance diffusion rate is determined by the net resistance of all diffusional components, the net diffusion being dominated by the single diffusion component with the lowest substance permeability. Thus, since a rate limiting membrane, although artificial, having a precise and reproducible permeability is used, the overall substance permeability coefficient may be maintained relatively constant.

Another important feature of the present invention is that the invention is capable of filtering the fluids noninvasively obtained from a human body. Fluids are filtered through the mucosal or artificial semipermeable membranes by the diffusion limiting properties described above. Therefore, by coordinating an appropriate mucosal or semipermeable membrane for the specific substances to be passed through the semipermeable membranes, substances can be filtered by the present invention to the exclusion of non-selected substances. The use of filtering can advance the accuracy of some analytical testing techniques whose resulting data concerning the presence of substances can be impaired by many materials that usually exist in plasma or serum.

Still another feature of the present invention is that means are provided for continually monitoring the substance receiving medium for the concentration of substances without removing the housing and the substance receiving medium from the mucosal membrane. Such continual monitoring means may take the form of at least one elongated tube which communicates between the substance receiving medium through a port in the housing and testing equipment. It can be understood that the removal of the housing and substance receiving medium from the mucosal membrane to test for the concentration of substances involves possible contamination and an obvious discontinuity between the passage of substances through the mucosal membrane to the substance receiving medium. The continual monitoring means may include a second elongated tube communicating with the housing by a port to replenish the substance receiving medium from a replenishing source.

It is, therefore, an object of the present invention to provide apparatus and methods for noninvasive blood substance monitoring which avoid the inconvenience and risk associated with traditional invasive blood substance monitoring techniques.

An additional object of the present invention is to provide apparatus and methods for noninvasive blood substance monitoring which provide accurate and reproducible correlation with actual blood substance levels.

Another important object of the present invention is to provide apparatus and methods for noninvasive blood substance monitoring which can be performed rapidly.

Also, another important object of the present invention is to provide apparatus and methods for noninvasive blood substance monitoring which do not lead to inaccurate results due to contamination of the monitored sample by substances such as saliva.

Yet another important object of the present invention is to provide apparatus and methods for noninvasively monitoring the concentration of substances in the blood which are not limited to certain individuals, but instead can be applied to a wide variety of individuals.

A further important object of the present invention is to provide apparatus and methods for noninvasively monitoring the concentration of substances in the blood which can be performed at a location, and at a point in time, where and when an individual is first required to be monitored for the concentration of substances. These and other objects and features of the present invention will become more fully apparent from the following description and appended claims, taken in conjunction with the accompanying drawings, or may be learned from the practice of the invention.

DETAILED DESCRIPTION OF THE PREFERRED EMBODIMENTS

The present invention is directed to novel methods and apparatus for noninvasive blood substance monitoring. Such noninvasive techniques avoid the inconvenience and risks associated with traditional invasive monitoring techniques for the accurate measuring of certain substances because blood does not need to be withdrawn from the individual.

According to the present invention, substances present in the blood of a subject are monitored noninvasively by correlation with the amount of the substance which permeates a mucosal membrane into a substance receiving medium over a predetermined time period ("subject" is defined in this application as comprising a person or animal). The preferred embodiment of the present invention employs a mucosal surface of the body, such as the buccal membranes lining the cheek, because mucosal surfaces are generally permeable to the substances.

I. THEORETICAL CONSIDERATIONS

According to the apparatus and methods within the scope of the present invention, substances diffuse from the submucosal interstitial fluid, which is in equilibrium with blood in capillary blood vessels perfusing the mucosal membrane, across the membrane into a substance receiving medium. From a theoretical viewpoint, the submucosal interstitial fluid is in equilibrium with blood in the capillary vessels and is considered a donor chamber, while the substance receiving medium is considered a receiver chamber. The donor chamber and the receiver chamber are separated by the mucosal membrane.

In the donor chamber, there is a finite concentration ($C_o$) of permeant corresponding to the substance. The permeant concentration in the receiver chamber is zero at an initial time t=0. If the concentration of the permeant in the donor chamber is kept constant ($C_o$) and the permeant concentration in the receiver chamber is much lower than $C_o$ for the entire experiment ("sink condition"), then the amount of the permeant in the receiver chamber as a function of time is approximated by:

$$Q(t) = A \cdot C_o \left[ \frac{Dt}{h} - \frac{h}{6} - \frac{2h}{\pi^2} \sum_{n=1}^{\infty} \frac{(-1)^n}{n^2} e^{-n^2\pi^2 Dt/h^2} \right]$$

and the diffusion lag time t(lag) is given by:

$$t(\text{lag}) = \frac{h^2}{6D}$$

and the flux of the permeant is given by:

$$\text{Flux}(t) = \frac{1}{A} \cdot \frac{dQ(t)}{dt}$$

where "Q(t)" is the mass of the permeant in the receiver chamber at time "t", "D" is the apparent diffusion coefficient of the permeant in the membrane, "h" is the thickness of the membrane, and "A" is the area of the membrane.

From the foregoing equations, it will be appreciated that both Q(t) and flux are proportional to $C_o$ at any time. Since both Q(t) and flux(t) are at all times proportional to the concentration of the substance in the blood, $C_o$, they can be used to monitor the blood substance concentration. However, in practice, precise measurement of Q(t) and the flux can only be made after t(lag) —since before t(lag), Q(t) is very low.

Figure 1:
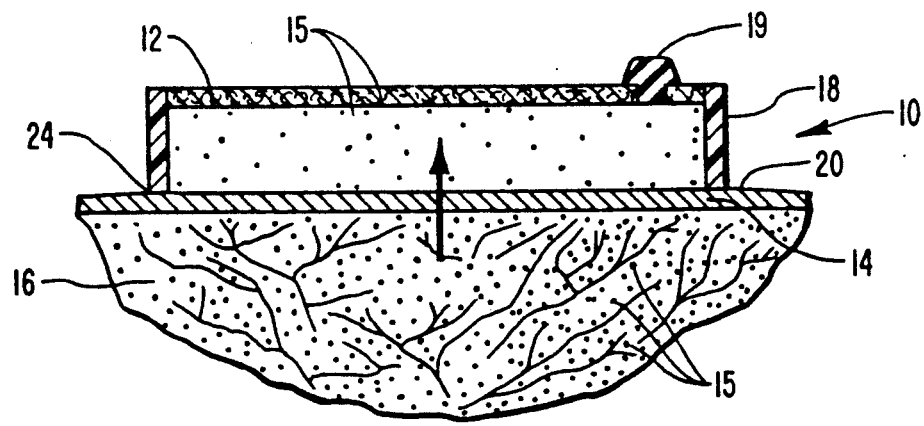
FIG. 1 is a cross-sectional schematic view of the noninvasive substance monitoring process of the present invention.

Reference is now made to FIG. 1 so that the function of the present invention can be better understood. The foregoing equations are valid in those situations where the D of substance receiving medium 12 is substantially greater than that of mucosal membrane 14. In such cases, substance receiving medium 12 acts as a substance "sink." The quantity of a substance diffusing from submucosal interstitial fluid 16, through the mucosal membrane 14, and into substance receiving medium 12, is determined by the most resistant layer along the diffusion pathway—i.e., the mucosal membrane 14.

On the other hand, if the diffusion coefficient of substance receiving medium 12 is substantially less than that of mucosal membrane 14, then the quantity of a substance entering the substance receiving medium is limited by substance receiving medium 12.

Figure 2:
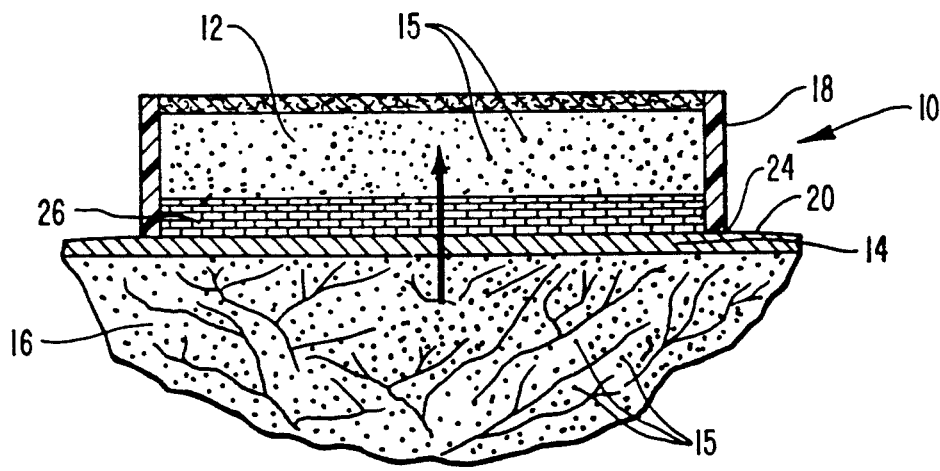
FIG. 2 is a cross-sectional schematic view of the noninvasive substance monitoring process of the present invention using a rate regulating membrane.

Referring now to FIG. 2, one or more additional regulating membranes 26 may be placed between the mucosal membrane 14 and the substance receiving medium 12 to achieve a rate regulating function. In this case, it is preferred that the permeability coefficient of rate regulating membrane 26 is significantly lower than that of mucosal membrane 14 and that of substance receiving medium 12. Thus, the quantity of a substance entering the substance receiving medium is limited or regulated by the most resistant layer of the substance diffusion pathway—i.e., rate regulating membrane 26.

From a theoretical viewpoint, a substance must diffuse through two membranes to enter the substance receiving medium: the mucosal membrane and the rate regulating membrane. The effective permeability coefficient of the combined membranes is given by:

$$P_T = P_M \cdot P_R / (P_M + P_R)$$

where "$P_T$", "$P_M$", and "$P_R$" are the permeability coefficients of the combined membrane, the mucosal membrane, and the rate regulating membrane, respectively. $P_R$ can be made precisely and reproducibly by modern techniques, while $P_M$ may vary from person to person, time to time, and even position to position within the same type of mucosal membrane.

The above equation suggests that if $P_R$ is significantly lower than $P_M$, $P_T$ will stay relatively stable despite variations in $P_M$. For example, if $P_R = \frac{1}{5} P_M$, a 30% variation in $P_M$ will only cause about a 6% variation in $P_T$. A stable and less varying permeability coefficient of the combined membranes enables accurate and consistent results even in the presence of relatively large variation in mucosal permeability.

In both of the above cases the quantity of a substance permeated into the substance receiving medium is given by $$Q(t) = C_o \cdot f(A, D_M, D_R, h_M, h_R, t)$$

where "$C_o$" is the concentration of the substance in the submucosal interstitial fluid or capillary blood vessels; "A" is the area of contact; "$D_M$" and "$D_R$" are diffusion coefficients of the substance in the mucosal membrane and in the rate regulating membrane, respectively; "$h_M$" and "$h_R$" are the thicknesses of the mucosal membrane and the rate regulating membrane, respectively; "t" is the time passed from the beginning of contact; and "f" is a complicated function of the above variables. This equation is valid at all conditions, even if the "sink condition" is not maintained.

From the above equation, it is evident that the quantity of a substance permeated into the substance receiving medium is proportional to the concentration of the substance in the donor chamber (submucosal interstitial fluid and capillary blood vessels) at any time, provided that other variables in the above equation are kept relatively constant.

In a broad sense, the apparatus of the present invention is directed to a substance receiving medium and to means for supporting the substance receiving medium against a mucosal membrane. Permeation enhancers added to the substance receiving medium may alter the diffusion coefficient of substance in those mucosal tissues, thereby increasing Q(t) and flux and reducing t(lag).

In those cases where permeation enhancers are needed, increasing the concentration or potency of the permeation enhancer significantly reduces the diffusion lag time. In fact, dramatically increasing the permeation enhancer concentration renders the lag time substantially negligible and enables rapid detection of the blood substance level noninvasively.

II. Monitored Substances of the Present Invention

The different types of substances which are routinely tested is quite diverse. One classification of the type of substances which are routinely tested are substances that naturally occur in a human body. This can include protein substances such as amino acids, urea, glucose, insulin, peptides, hormones and endorphones.

Another classification of the type of substances which are routinely tested are substances which are introduced into a human body from an external source. These types of substances may be produced naturally or synthetically. Examples of some types of externally derived substances include alcohol, narcotics, nitroglycerin, and intravenous anesthetics.

In order for the present invention to operate effectively, it is necessary that the substance be capable of permeating the mucosal membrane either alone or in combination with a suitable permeation enhancer. For purposes of illustrating the applicability of the present invention in different envisionments, a detailed discussion is provided regarding noninvasive monitoring of blood levels of alcohol, glucose, and intravenous anesthetics.

A. Alcohol

In recent years blood testing has been used as a technique to be employed in other than medical situations such as an investigative device used to determine if an individual is legally impaired by alcohol.

Driving while under the influence of alcohol has become a major concern in the United States. It is the number one cause of death and accident on our highways. Individuals who do so jeopardize not only their own lives due to a decreased reflex response and an impaired thought process, but they also jeopardize the lives of those individuals with whom they may come in contact. Athletics, industry, bars, rehabilitation centers, and common carriers are also areas subject to testing for alcohol.

The term "alcohol" is a chemical term which is broadly defined as a hydroxyl derivative of hydrocarbons. More commonly, alcohol is a colorless volatile flammable liquid, $C_2H_6O$, that is the intoxicating agent in fermented and distilled liquors, and called ethyl alcohol. Alcohol is used also as a solvent. The present invention would be directed to noninvasively monitoring the presence of alcohol, as it is broadly defined, in individuals.

B. Glucose

According to another embodiment of the present invention, blood glucose is monitored noninvasively by causing glucose to diffuse across epithelial membranes and then capturing and measuring that glucose for correlation to determine the blood glucose level. The monitoring of glucose levels in blood can be used to monitor diabetes in an individual. Diabetes is a disorder of carbohydrate metabolism characterized by elevated blood sugar (hyperglycemia), sugar in the urine (glycosuria), excessive urine production (polyuria), excessive thirst (polydipsia), and increase in food intake (polyphagia).

C. Substances of Abuse

According to yet another embodiment of the present invention, substances of abuse are monitored noninvasively by causing the abused substance to diffuse across epithelial membranes and then capturing and measuring those abused substances for correlation to determine the concentration of the abused substances in the blood. The category of abused substances can include narcotics such as cocaine, nevertheless, those abused substances which fall within the category of the present invention are known to those skilled in the art. Preferably, those abused substances which are not readily measured in saliva, and thus are more quantitatively defined, are typical of the substances measured by the present invention.

D. Intravenous Anesthetics

The term "intravenous anesthetics" is quite broad in its definition. The present invention has applicability to a variety of drugs affecting the central nervous system. For example, the present invention may easily be utilized in the administration of opioid agonists (such as fentanyl, alfentanil, sufentanil, lofentanil, and carfentanil), opioid antagonists (such as naloxone and nalbuphene), butyrophenones (such as droperidol and haloperidol); benzodiazepines (such as valium, midazolam, triazolam, oxazolam, and lorazepam); GABA stimulators (such as etomidate); barbiturates (such as thiopental, methohexital, thiamazol, pentobarbital, and hexobarbital); di-isopropyl-phenols drugs (such as diprivan); and other central nervous system-acting drugs such as levodopa. It will be appreciated that other drugs may also be utilized within the scope of the present invention either singly or in combination.

Table 1 lists some of the intravenous anesthetics which are suitable for passage to the substance receiving medium of the present invention, as well as some of the characteristics of those drugs.

TABLE 1

| GENERIC DRUG | DRUG CLASS | DOSE RANGE |
| --- | --- | --- |
| methohexital | barbiturate | 10–500 mg |
| pentobarbital | barbiturate | 50–200 mg |
| thiamylal | barbiturate | 10–500 mg |
| thiopental | barbiturate | 50–500 mg |
| fentanyl | opioid agonist | 0.05–5 mg |
| alfentanil | opioid agonist | 0.5–50 mg |
| sufentanil | opioid agonist | 5–500 μg |
| lofentanil | opioid agonist | 0.1–100 μg |
| carfentanil | opioid agonist | 0.2–100 μg |
| naloxone | opioid antagonist | 0.5–5 mg |
| nalbuphene | opioid antagonist | 1–50 mg |
| diazepam | benzodiazepine | 1–40 mg |
| lorazepam | benzodiazepine | 1–4 mg |
| midazolam | benzodiazepine | 0.5–25 mg |
| oxazepam | benzodiazepine | 5–40 mg |
| triazolam | benzodiazepine | 0.25–2.5 mg |
| droperidol | buterophenone | 1–20 mg |
| haloperidol | buterophenone | 0.5–10 mg |
| propanidid | eugenol | 1–10 mg |
| etomidate | GABA stimulator | 5–60 mg |
| propofol | substituted phenol | 3–200 mg |
| ketamine | phencyclidine | 5–300 mg |
| diprivan | substituted phenol | 5–20 mg |

Drugs having effects on the cardiovascular and renal vascular systems may also be monitored using the noninvasive procedures of the present invention. A few examples of such drugs are identified in Table 2.

TABLE 2

| GENERIC DRUG | DRUG CLASS | DOSE RANGE |
| --- | --- | --- |
| Bretylium | antiarrhythmic | 50–500 mg |
| Captopril | ACE inhibitor | 25–75 mg |
| Clonidine | antihypertensive | 0.1–0.5 mg |
| Dopamine | renal vascular | 0.5–5 mg |
| Enalapril | ACE inhibitor | 5–15 mg |
| Esmolol | antihypertensive/angina | 100–250 mg |
| Furosemide | diuretic | 20.0–100 mg |
| Isosorbide | angina | 2.5–40 mg |
| Labetolol | antihypertensive | 100–400 mg |
| Lidocaine | antiarrhythmic | 50–250 mg |
| Metolazone | diuretic | 5–50 mg |
| Metoprolol | antihypertensive | 25–100 mg |
| Nadolol | antihypertensive | 40–160 mg |
| Nifedipine | antihypertensive/ angina/vasodilator | 10–40 mg |
| Nitroglycerin | antihypertensive/angina | 0.4–1.0 mg |

TABLE 2-continued

| GENERIC DRUG | DRUG CLASS | DOSE RANGE |
|---|---|---|
| Nitroprusside | hypotensive | 10–50 mg |
| Propranolol | antihypertensive/angina | 0.1–50 mg |

In addition to the foregoing, there are many other substances which can be monitored by the noninvasive procedures of the present invention. Exemplary of such drugs are those identified in Table 3.

TABLE 3

| GENERIC DRUG | DRUG CLASS | DOSE RANGE |
|---|---|---|
| Benzquinamide | antiemetic | 25–100 mg |
| Meclizine | antiemetic | 25–100 mg |
| Metoclopramide | antiemetic | 5–20 mg |
| Prochlorperazine | antiemetic | 5–25 mg |
| Trimethobenzamide | antiemetic | 100–2500 mg |
| Clotrimazole | antifungal | 10–20 mg |
| Nystatin | antifungal | 100,000–500,000 units |
| Carbidopa | antiparkinson | with levodopa 10–50 mg |
| Levodopa | antiparkinson | 100–750 mg |
| Sucralfate | antisecretory | 1–2 grams |
| Albuterol | bronchodilator | 0.8–1.6 mg |
| Aminophylline | bronchodilator | 100–500 mg |
| Beclomethasone | bronchodilator | 20–50 µg |
| Dyphylline | bronchodilator | 100–400 mg |
| Epinephrine | bronchodilator | 200–500 µg |
| Flunisolide | bronchodilator | 25–50 µg |
| Isoetharine | bronchodilator | 170–680 µg |
| Isoproterenol HCl | bronchodilator | 60–260 µg |
| Metaproterenol | bronchodilator | 0.65–10 mg |
| Oxtriphylline | bronchodilator | 50–400 mg |
| Terbutaline | bronchodilator | 2.5–10 mg |
| Theophylline | bronchodilator | 50–400 mg |
| Ergotamine | antimigraine | 2–4 mg |
| Methysergide | antimigraine | 2–4 mg |
| Propranolol | antimigraine | 80–160 mg |
| Suloctidil | antimigraine | 200–300 mg |
| Ergonovine | oxytocic | 0.2–0.6 mg |
| Oxytocin | oxytocic | 5–20 units |
| Desmopressin acetate | antidiuretic | 10–50 µg |
| Lypressin | antidiuretic | 7–14 µg |
| Vasopressin | antidiuretic | 2.5–60 units |
| Insulin | antihyperglycemic | 1–100 units |

In addition to the foregoing drugs, certain macromolecular drugs (such as β-endorphin, enkephalins, bradykinin, angiotensin I, gonadotropic hormones, adrenocorticotropic hormone (ACTH), calcitonin, parathyroid hormone, and growth hormone), polysaccharides (such as heparin), antigens, antibodies, and enzymes may be adapted for passage through transmucosal tissues within the scope of the present invention.

In summary, it will be appreciated that a wide variety of drugs can be used within the scope of the present invention. At the same time, several benefits are provided. Efficient monitoring of the drug is provided while at the same time invasive techniques are avoided. The drug can also be monitored on a repeated basis so that the drug effect produced in the human body is precisely controlled.

Although specific reference has been made to certain types of substances which naturally occur in a human body, or natural or synthetic substances which are introduced to a human body by an external source, it must be remembered that the present invention is not limited as such. Any substance which may be present in blood and may diffuse into a receiving medium, as defined herein, may be employed.

III. Preferred Apparatus of the Present Invention

Figure 3:
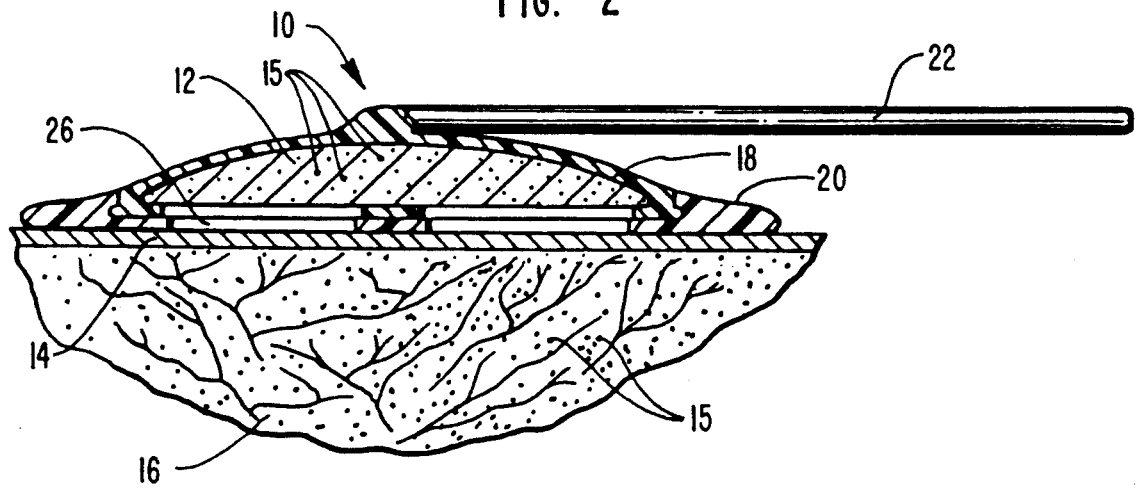
FIG. 3 is a cross-sectional view of one possible apparatus within the scope of the present invention.

Reference is now made to FIG. 3 wherein one possible apparatus within the scope of the present invention is illustrated in a cross-sectional view. Noninvasive substance monitoring device 10 includes substance receiving medium 12 which is positioned against mucosal membrane 14. Substance receiving medium 12 may include a permeation enhancer (not shown) for improving the permeability of mucosal membrane 14 to a substance 15. Substances 15 monitored within the scope of the present invention are preferably soluble in substance receiving medium 12. Hence, water is one currently preferred substance receiving medium 12. It is to be understood, however, that alternative media in which substances 15 are soluble may also be used as a substance receiving medium 12 within the scope of the present invention.

Other compositions which dissolve substances 15 may also be suitably used as substance receiving media 12 within the scope of the present invention. Further, suitable substance receiving media 12 should not unfavorably react with a substance 15 or any permeation enhancers which may be used. Substance receiving medium 12 should not interfere with the measurements of the concentrations of substances 15. It should also be nontoxic to the mucosal membrane and chemically and physically stable (e.g., does not degrade and is nonvolatile).

It is also within the scope of the present invention to provide a substance receiving medium 12 containing a complexing agent which selectively combines with substance 15 to form an insoluble product. If such a complexing agent is included in the substance receiving medium 12, then the resulting substance complex is preferably detectable using known analytical techniques. The resulting insoluble substance product may facilitate quantifying the concentration of substance 15.

The driving force behind the diffusion of substance 15 into substance receiving medium 12 is the concentration gradient of substance 15 between the submucosal interstitial fluid 16 and substance receiving medium 12. The resistance to the permeation is determined by the permeability of mucosal membrane 14, the permeability of substance receiving medium 12, or some other rate regulating membrane or media.

The substance receiving medium 12 preferably has a relatively low concentration of substance 15 for the entire duration of measurement with respect to that in submucosal interstitial fluid 16 and capillary blood vessels, yet at the end of the measurement, the concentration of the substance in substance receiving medium 12 is high enough to be measured precisely. If a permeation enhancer is employed, the substance permeability of mucosal membrane 14 may increase and a greater amount of substance 15 may diffuse into substance receiving medium 12.

The actual amount of substance 15 which diffuses into substance receiving medium 12 depends upon many factors such as the type of mucosal membrane (hard pallete, buccal, sublingual, tracheal, bronchial, and the like) if required, the enhancer used, the enhancer concentration, the contact exposure time, the type of substance receiving medium 12, the mucosal membrane surface area in contact with substance receiving medium 12, intimacy of contact between substance receiving medium 12 and the membrane, and the solubility of substance 15 in substance receiving medium 12. Based upon the teaching herein, it is within the skill of the art to balance the foregoing factors in order to cause the desired amount of a substance 15 to diffuse into substance receiving medium 12 under particular circumstances or measurement criteria.

The amount of a substance 15 which must diffuse into substance receiving medium 12 in order to be accurately measured depends upon the sensitivity of the analytical detection methods used. Currently, some techniques detect substances having a concentration as low as 0.2 ng/ml, providing suitable results for the diagnostic methods within the scope of the present invention. Other criteria useful in selecting a suitable substance detection method include the method's specificity to a substance 15 and convenience of the method.

One technique which may be employed in the present invention utilizes a colorimetric or UV absorption determination. The substance 15 to be measured reacts with certain chemicals known to those skilled in the art. The product(s) of the reaction has absorption band(s) in certain wavelengths in either the visible or UV wavelength ranges. The absorbance at each wavelength is proportional to the substance concentration.

Another technique which may be employed in the present invention is fluorimetry. Fluorescence is the emission of light by a fluorochrome that absorbs light at a lower wavelength.

Fluorochromes may also be attached chemically to antibodies which are directed to specific substances 15 which may be present in substance receiving medium 12. The attachment of the fluorochrome does not alter the specificity of the antibody significantly, but makes it possible to detect the antibody adsorbed to a substance. The fluorescent antibody that binds to substances 15 can then be measured to determine the concentration of substances 15 in substance receiving medium 12. The percentage binding of antibody to substance 15 is determined by such techniques as polarization rotation.

The foregoing techniques of UV light detection and fluorimetry, are provided as an example of the types of methods that are available in the art to detect the concentration of substances 15 in fluids. The equipment and their application to the present invention of these two techniques would be known to one skilled in the art. In addition, the present invention is not limited to these two techniques, but instead includes any other techniques known to those skilled in the art which could detect the concentration of substance 15, as defined herein, in substance receiving medium 12.

Convenience of the substance concentration detecting methods must be emphasized as an important criteria of the present invention. Methods which do not readily afford accommodation inevitably give results having a higher probability of being incorrect. Also, the more convenient a method is, the more likely a person unfamiliar with the method will be able to adapt and use the method. Therefore, an increased number of individuals will be able to operate the present invention.

The present invention further comprises means for supporting and isolating substance receiving medium 12 such that substance receiving medium 12 may be positioned against mucosal membrane 14 apart from contaminating sources. The supporting and isolating means comprises a housing 18 which is illustrated in FIG. 3. Although the described embodiments set forth the best mode presently contemplated for the practice of the present invention, they are to be considered in all respects only as illustrative and not restrictive.

Housing 18 encloses substance receiving medium 12 and protects substance receiving medium 12 from potential substance contamination sources such as saliva. Saliva can accumulate in an area that is to be sampled and the addition could increase the concentration of substance 15 in the sample. Therefore, in order to obtain precise and reliable measurements from a substance containing sample, it is necessary to isolate the sample from contaminating sources such as saliva.

Housing 18 is preferably constructed of a material which is nontoxic, chemically stable, nonreactive with substance 15 and the permeation enhancers used, and inexpensive. Also, housing 18 is not permeable to substances being measured and the substance receiving medium 12. Suitable materials include: polypropylene, polyethylene, polyolefins, polyamides, polycarbonates, vinyl polymers, and other similar materials known in the art.

Housing 18 may take many different shapes; however, the housing should define a chamber for holding a quantity of substance receiving medium 12 and provide an opening such that substance receiving medium 12 may be placed directly against, or have direct contact with, mucosal membrane 14.

Housing 18 may also include an access port 19, as illustrated in FIG. 1, through which substance receiving medium 12 may be introduced into the housing or through which substance receiving medium 12 may be directly tested for substance 15 or removed for external testing while housing 18 is maintained in position against mucosal membrane 14.

The present invention also includes means for temporarily positioning substance receiving medium 12 against a mucous membrane. In one embodiment, the temporarily positioning means includes a handle 22. When housing 18 is used in connection with measuring substance diffusion across mucosal membrane 14, such as those in the mouth, the temporarily positioning means advantageously includes a handle 22 which may optionally be attached, permanently or temporarily, to housing 18 to facilitate placement and removal of the apparatus. Handle 22 is particularly desirable to provide a user with control over placement and removal. It can also be helpful to maintain housing 18 in contact with the mucosal tissues if an adhesive is not employed.

The present invention further includes means for joining substance receiving medium 12 to a mucosal membrane. In one embodiment, the joining means includes flanges 20 located about the periphery of housing 18 for receiving an adhesive, such as a hydrogel, so that housing 18 may be maintained in position against mucosal membrane 14.

It should be noted that the apparatus within the scope of the present invention may not require a housing as illustrated in FIG. 3. The means for joining substance receiving medium 12 to mucosal membrane 14 may include the use of a hydrogel. For example, it has been found that certain kinds of hydrogels not only serve as a suitable substance receiving medium 12, but also adhere well to mucosal membranes. Thus, flanges 20 would not be necessary since the hydrogel itself serves as both substance receiving medium 12 and adhesive.

When a hydrogel is used as a support, the bioadhesive hydrogel itself joins substance receiving medium 12 against mucosal membrane 14. In the context of a hydrogel, substance receiving medium 12 corresponds to an aqueous portion of the hydrogel, whereas a cellulose frame or other material forming the hydrogel provides the necessary support of substance receiving medium 12. Hence, substance receiving medium 12 within the scope of the present invention may be supported in a hydrogel.

Importantly, many hydrogels are inherently sticky. Such bioadhesive hydrogels adhere directly to mucosal tissues. Cellulose, including hydroxypropylcellulose and other cellulose derivatives known in the art, carbopol, gelatin, and other known materials which produce hydrogels, may be used within the scope of the present invention.

Other materials which perform substantially the same function as hydrogels may also be used. For example, creams, emulsions, suspensions, and other solid and semisolid media may also serve as adhesive and substance receiving medium 12. A sponge-like embodiment may also act accordingly.

Whether a hydrogel or other substance is used to serve as both substance receiving medium 12 and adhesive, it is important that substance receiving medium 12 be safely supported and maintained in contact with the mucosal tissues for sufficient time to effect the diffusion of substance 15 across mucosal membrane 14.

In one embodiment within the scope of the present invention, means for sealing the hydrogel or other substance receiving media 12 from potential contaminants such as saliva is provided. The sealing means may comprise a nonpermeable membrane, such as a thin plastic layer, which covers the hydrogel or other substance receiving media 12 to protect substance receiving media 12 from potential contamination. A housing, as described above, would also suitably protect and isolate the hydrogel. In addition, a housing (and optionally a handle) would facilitate positioning and removal of the hydrogel.

Depending on the thickness and total surface area of the hydrogel or other substance receiving medium 12, the edges may not need to be covered or sealed. In this regard, lateral edges 24, illustrated in FIGS. 1 and 2, may not be necessary. Of course, if there is a significant risk of substance contamination from saliva or foods, then it would be important to include lateral edges 24.

It will be appreciated that there are many other possible embodiments within the scope of the present invention which perform substantially the same function as the embodiment illustrated in FIG. 3. For example, clamps, buccal tapes, matrix patch-type designs, and other similar designs described in the patent literature may be used within the scope of the present invention.

IV. Use of the Present Invention

In use, substance receiving medium 12 is preferably positioned directly against mucosal membrane 14. Before positioning substance receiving medium 12, however, care should be taken to cleanse the surface of mucosal membrane 14 to be tested. The step of cleansing could remove any possible contaminants from the surface of mucosal membrane 14 which may alter the testing and lead to inaccurate results.

The surface of mucosal membrane 14 may be cleansed in a number of ways. The surface may be cleansed by manually applying a gauze pad, treated with cleansing solution, to wipe away any contaminants. Also, some type of cleansing apparatus could be placed against the surface which does not require any individual manipulation. Once the surface of mucosal membrane 14 is cleansed, substance receiving medium 12 is applied. In those cases where a permeation enhancer is included in substance receiving medium 12, the permeation enhancer contacts mucosal membrane 14 and increases the substance permeability of mucosal membrane 14.

Various mucosal membranes may be utilized within the scope of the present invention, although some membrane surfaces are more preferable than others. The selection of a suitable mucosal membrane depends upon a number criteria, such as substance permeability with and without a given quantity of enhancer, degree of irritation caused by the enhancer, lag time, convenience (e.g., buccal membrane is more accessible than nasal and rectal membranes), and the degree of vascularization.

In the preferred embodiment of the present invention, buccal mucosal membrane surfaces are preferred over all others because the amount of surface area available to accommodate the present invention is greater and more accessible than other mucosal membrane areas.

After sufficient time delay, substance receiving medium 12 is removed and analyzed for the concentration of substance 15 using conventional analytical techniques. Variables affecting sufficient exposure time include: substance detecting sensitivity, permeability, lag time, enhancer concentration, substance receiving medium 12 surface contact area to volume ratio, and temperature. While these variables affecting sufficient exposure time exist, the preferred embodiment of the present invention minimizes these variables by employing methods which have high substance detecting sensitivity, measure areas which have a high surface contact area to volume ratio, are highly permeable and measure at a temperature range that has been experimentally found to be ideal.

There are many different techniques known in the art for determining the concentration of a substance in blood. For example, alcohol concentration can be determined with a colorimetric determination. (Sigma Diagnostic Kit No. 332). In the preferred embodiment of the present invention in which alcohol was detected transmucosally, the alcohol which diffused across the mucosal membrane into the receiving medium has been measured using a standard Substance Diagnostic Kit Solution obtained from Sigma Chemical Co.(Sigma Diagnostic Kit No. 332-UV).

The Diagnostic Kit was modified to increase the detecting sensitivity to 0.1 $\mu g/ml$ by increasing the substance specimen to Diagnostic Kit solution ratio. Also, the procedure was modified slightly by using an alcohol sample solution instead of blood. Alcohol concentration as low as 0.1 $\mu g/ml$ was accurately detected using this technique.

Because the alcohol concentration within the alcohol receiving medium is proportional to the individual's actual blood substance level, once the alcohol within substance receiving medium 12 is determined the actual blood alcohol level may be quickly calculated.

For user convenience, a color indicator may be incorporated into the alcohol receiving medium. In this way, the alcohol concentration may be quickly determined by comparing any color change (not necessarily in the visible light spectrum) of the alcohol receiving medium against a standard color chart. Commercially available indicators include those known to those skilled in the art.

V. Additional Uses of the Present Invention

An additional use of the present invention, which has not been discussed, is the use of the present invention as a filter. The present invention can be modified to be employed with the principles of diffusion to filter substances traveling into substance receiving medium 12 such that only the substance is passed from the mucosal membrane to substance receiving medium 12. The filtering process is similar to dialysis in that some substances permeate from submucosal interstitial fluid 16 to substance receiving medium 12 without bulk transport of fluids. The filtering of substances can purify the substance or simply separate substances from one another.

It should be emphasized that the filtration process is the natural result of this technique. It happens with or without an artificial membrane. In the case of the latter, most substances in plasma that would interfere with any analysis are filtered out by the mucosal membrane itself due to their sizes and hydrophilicity. In the case of the former, the artificial membrane may provide additional filtration.

Figure 4:
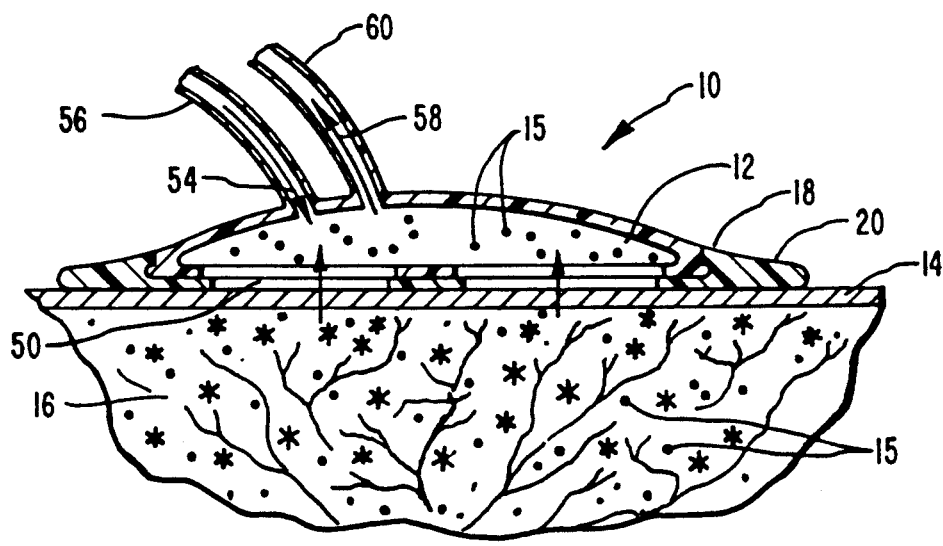
FIG. 4 is a cross-sectional view of another possible apparatus within the scope of the present invention, featuring the filtering and continual monitoring aspects.

In one embodiment of the present invention, as illustrated in FIG. 4, means for filtering are placed adjacent to substance receiving medium 12 in order to selectively allow substances to permeate from submucosal interstitial fluid 16 to substance receiving medium 12. As an example which is not meant to limit the scope of the present invention, the filtering means comprises an artificial semipermeable membrane 50 which is placed between substance receiving medium 12 and the submucosal interstitial fluid 16 to be filtered. Semipermeable membrane 50 can be constructed such that the semipermeable membrane 50 selectively allows some substances 15, and prevents other substances 15, to travel through semipermeable membrane 50 from the submucosal interstitial fluid 16 to substance receiving medium 12.

In one embodiment, semipermeable membrane 50 is constructed of a predetermined pore size. The diameter of the pore size specifies the size of the particles that are capable of passing therethrough. Particles of a size larger than the pore size are prevented from passing therethrough. Alternatively, the semipermeable membrane 50 may be structured such that the semipermeable membrane 50 chemically filters substances therethrough.

It should be pointed out, as previously discussed, that the filtering means comprises the mucosal membrane 14, or other membrane which naturally filters substances. In this instance, the mucosal membrane 14 is placed adjacent substance receiving medium 12, and substances 15 are allowed to travel from the bloodstream in a patient to substance receiving medium 12. The mucosal tissue 14 acts as a natural filter, the filtration prohibiting the entrance of compounds found in blood to substance receiving medium 12 which may interfere with assaying for the substance 15.

The present invention also comprises means for taking continual measurements of the concentration of substances in substance receiving medium 12. The continual measurement means obviates the need to take a measurement of substance receiving medium 12 by removing substance receiving medium 12 from the mucosal membrane 14 and subjecting it to possible contaminating sources. Instead substance receiving medium 12 is tested on a repeated basis, making adjustments for prior readings without removing substance receiving medium 12 from the mucosal membrane 14.

In one embodiment, and as illustrated in FIG. 4, the continual measurement means comprises an elongated tube 54 which communicates between the housing 18 and testing equipment (not shown) such as a fluorimeter. A sample of substance receiving medium 12 is transferred to the testing equipment through a port 56 in housing 18 along the elongated tube 54. Substance receiving medium 12 is driven along the elongated tube 54 from housing 18 to the testing equipment by means of pressure, either positive or negative.

The continual measurement means further comprises a second elongated tube 58 which replenishes substance receiving medium 12 to compensate for the aliquot of substance receiving medium 12 which was removed for testing. The second elongated tube 58 communicates between a replenishing source of substance receiving medium 12 and existing substance receiving medium 12 through a second port 60 in housing 18. The movement of substance receiving medium 12 from the replenishing source to housing 18 is by pressure, either positive or negative.

The continual measurement means still further comprises means for regulating the movement of substance receiving medium 12 between the housing 18 and the testing equipment or the replenishing source. In one embodiment, the regulating means comprises controls, either mechanical or computer derived, known to those skilled in the art which dictates the specific amount of fluid to travel along the first and second elongated tubes.

VI. EXAMPLES

The use of the methods for noninvasively monitoring blood substance concentrations within the scope of the present invention will be further clarified by a consideration of the following examples, which are intended to be purely exemplary of the use of the invention and should not be viewed as a limitation on any claimed embodiment.

EXAMPLE 1

In this example, blood alcohol was monitored noninvasively in a human subject. The subject was an oriental male of 32 years of age who had consumed two cans of beer prior the beginning of the experiment.

A diffusion cell was employed having an open bottom designed to be placed on the subject's buccal mucosa and an open top through which alcohol receiving solution was added and removed. The area of the cell's open bottom was 1.4 cm$^2$. The diffusion cell was placed on the subject's buccal mucosa.

At time t=0, 0.8 ml of a alcohol receiving solution was pipetted into the cell through the cell's open top. The alcohol receiving solution was distilled water. The substance receiving solution was in direct contact with the buccal mucosa through the open bottom end of the diffusion cell.

One 0.4 ml of solution was withdrawn from the cell after 1.5 minutes. At the same time, 1.0 ml of blood was withdrawn from the brachial vein of the subject to act as a control. The samples were then centrifuged for 15 minutes and the supernatant placed in separate vials and diluted with water to bring the alcohol concentration into a range suitable for an assay. Then, 0.3 ml of the sample from the diffusion cell was placed in a glass vial containing 0.1 ml of the Sigma Diagnostic Kit Solution for alcohol (No. 332). The resultant 0.4 ml solution was incubated at room temperature for exactly 18 minutes. After incubation, the 0.4 ml solution was placed in a 1 cm path length cuvette cell. The absorbance of the mixture at 340 nanometers was measured by a colorimeter (Milton Roy, Spectronic 21).

The relationship between the alcohol concentration in the sample and the absorbance is given by the following equation:

$$C(\mu g/ml) = A + B \times \text{Absorbance}$$

where A and B are constants determined by testing standard alcohol concentration solutions. The substance concentration in each sample, and from which the total amount of alcohol permeated across the buccal mucosa at a given time, can thus be obtained. The experimental results of Example 1 are shown graphically in FIG. 5.

Figure 5:
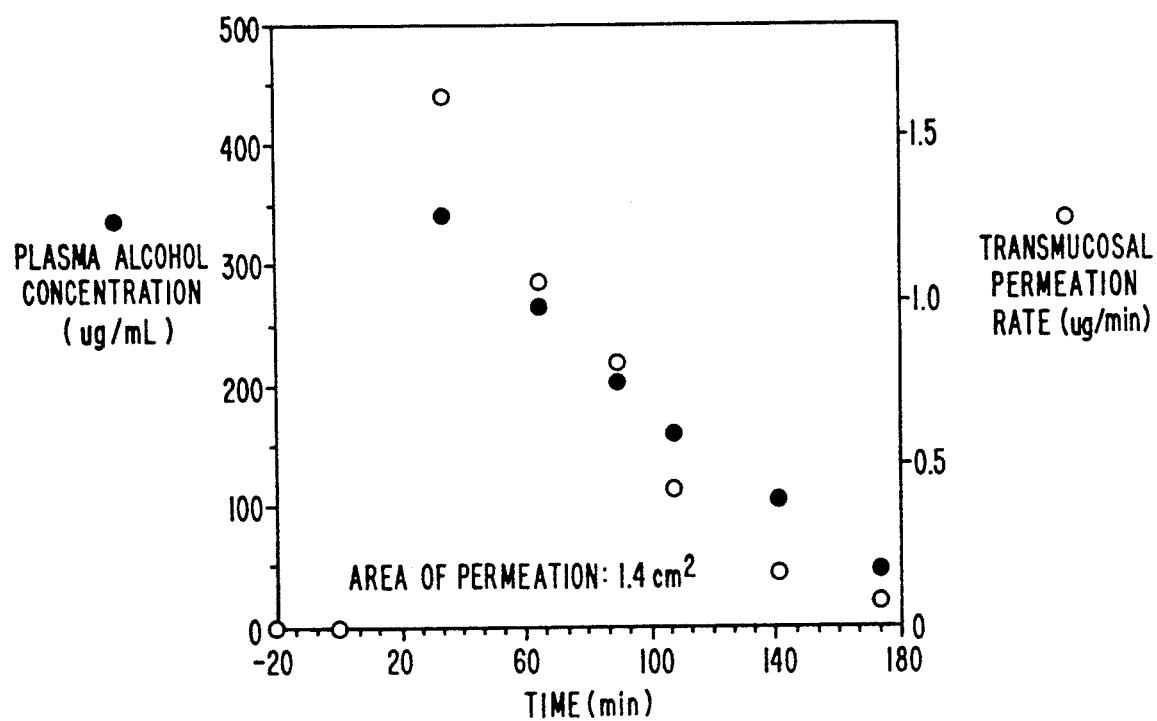
FIG. 5 is a graph of the alcohol concentration in plasma ($\mu g/ml$) versus time and transmucosal permeation rate ($\mu g/min$) versus time for the results of Example 1.

As it can be seen in FIG. 5, the plasma alcohol concentration and the transmucosal permeation rate declined over a period of time in a similar linear progression. From a high point, approximately 30 minutes after consumption of the liquor, the alcohol level of the individual decreased from approximately 300 ng/ml to almost 30 ng/ml 175 minutes after consumption of the liquor. Likewise, the transmucosal permeation rate declined from about 1.7 $\mu$g/min 30 minutes after the consumption of the liquor to almost 0.1 $\mu$g/min within about 175 minutes after consumption of the liquor.

The actual blood alcohol level monitored by taking blood samples from an intravenous catheter placed in the brachial vein were determined in the same way as described. The alcohol concentration in the blood samples were determined by the enzymatic, colorimetric technique described above (a modified Signa Diagnostic Kit No. 332-UV).

This method of monitoring blood alcohol allowed a quantitative analysis of small changes in the amount of alcohol in the patient's blood at any given time. The monitoring was quick and reliable. A direct correlation existed between the dose of alcohol the patient was given and the amount of alcohol which registered via the monitoring process.

EXAMPLE 2

Figure 6:
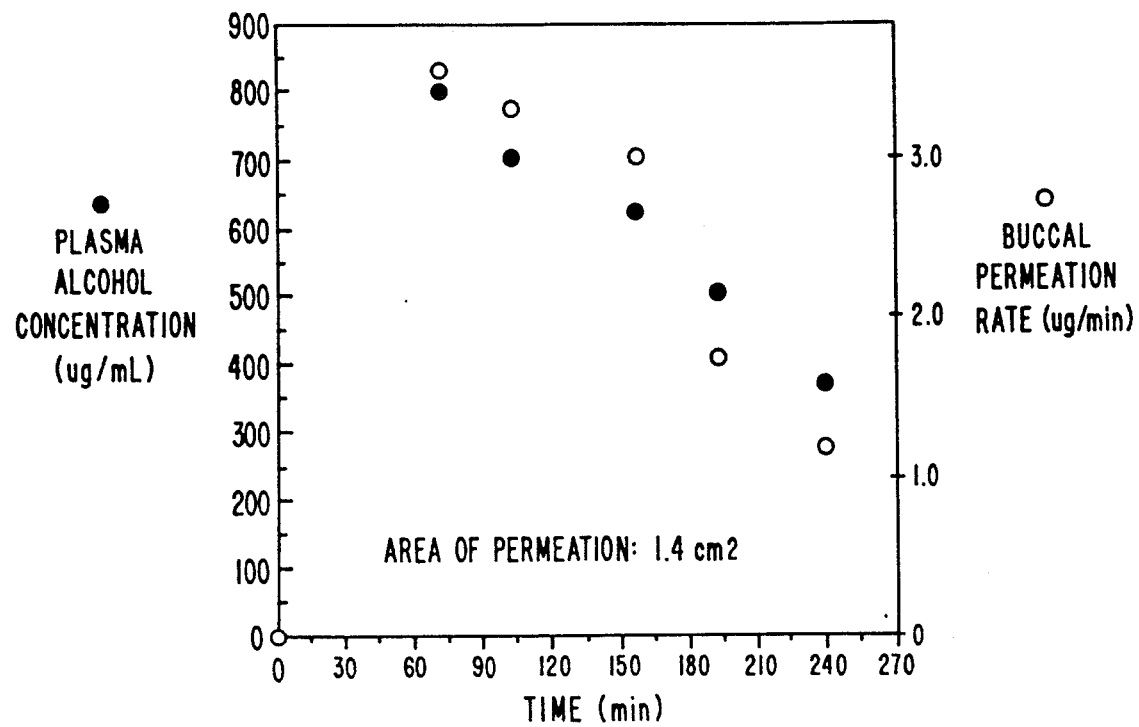
FIG. 6 is a graph of the alcohol concentration in plasma ($\mu g/ml$) versus time and buccal permeation rate ($\mu g/min$) versus time for the results of Example 2.

Blood alcohol was monitored noninvasively in a laboratory subject according to the procedure of Example 1, except that the test subject was an caucasian female of 22 years of age. Additionally, the test subject consumed 140 ml of gin prior to the beginning of the experiment as opposed to the two cans of beer consumed by the individual in Example 1. The experimental results of Example 2 are shown graphically in FIG. 6.

Similar to the results in FIG. 5, the serum alcohol concentration and the buccal permeation rate declined over a period of time in a similar linear progression. From a high point, approximately 60 minutes after the consumption of the liquor, the serum alcohol concentration of the individual decreased from approximately 800 $\mu$g/ml to almost 360 $\mu$g/ml about 240 minutes after consumption of the liquor. Likewise the buccal permeation rate declined from about 3.5 $\mu$g/min approximately 90 minutes after the consumption of the liquor to almost 1.2 $\mu$g/min 240 minutes after consumption of the liquor.

EXAMPLE 3

Figure 7:
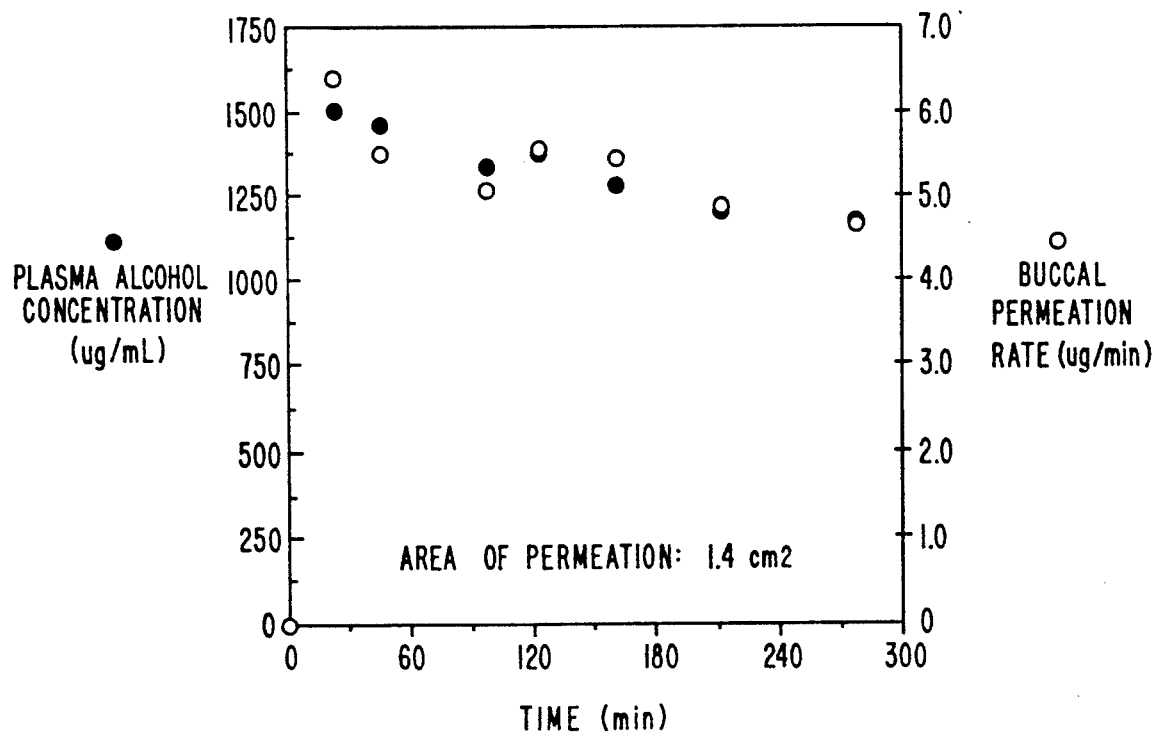
FIG. 7 is a graph of the alcohol concentration in plasma ($\mu g/ml$) versus time and buccal permeation rate ($\mu g/min$) versus time for the results of Example 3.

Blood alcohol was monitored noninvasively in a laboratory subject according to the procedure of Example 1, except that the test subject was an caucasian male of 21 years of age. Additionally, the test subject consumed 300 ml of gin prior to the beginning of the experiment as opposed to the two cans of beer consumed by the individual in Example 1. The experimental results of Example 3 are shown graphically in FIG. 7.

Similar to the results in FIG. 5, the serum alcohol concentration and the buccal permeation rate declined over a period of time in a similar linear progression. From a high point, approximately 30 minutes after the consumption of the liquor, the serum alcohol concentration of the individual decreased from approximately 1500 $\mu$g/ml to almost 1200 $\mu$g/ml 280 minutes after consumption of the liquor. Likewise the buccal permeation rate declined from about 6.4 $\mu$g/min approximately 30 minutes after the consumption of the liquor to almost 4.7 $\mu$g/min about 280 minutes after consumption of the liquor.

The results of examples 1-3 demonstrated a clear relationship between the buccal permeation rate and the plasma alcohol level for the tested individuals. The results indicated the buccal permeation rate and the plasma alcohol level followed a straight line correlation despite the age, gender, and ethnic differences between the tested individuals.

Figure 8:
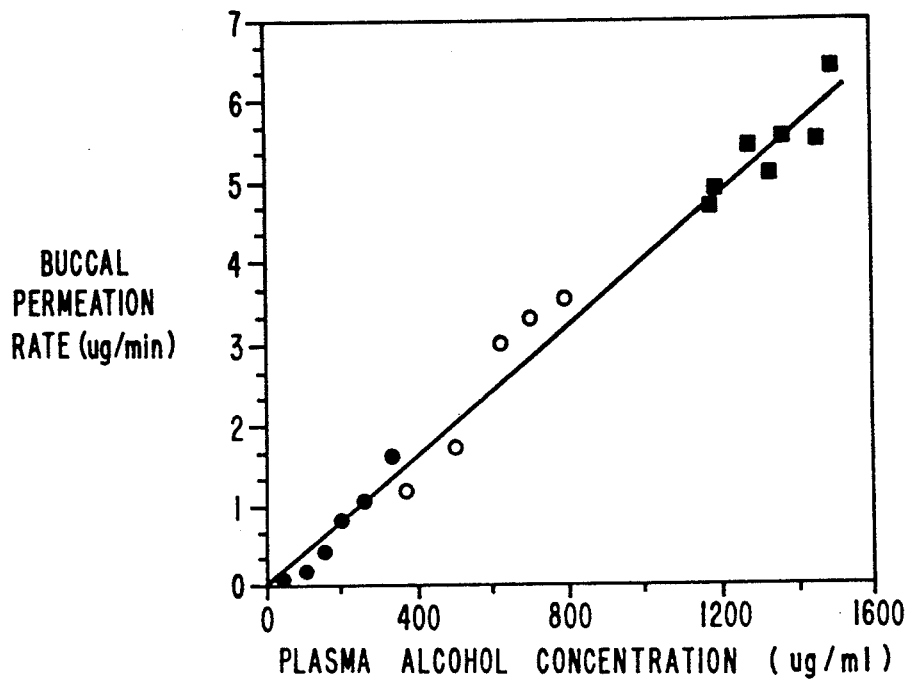
FIG. 8 is a graph of the alcohol concentration in plasma ($\mu g/ml$) versus time and buccal permeation rate ($\mu g/min$) versus time for the results of Examples 1-3.

The results of examples 1-3 were placed into a plot of the buccal alcohol permeation rate vs. plasma alcohol concentration in FIG. 8. A straight line was obtained from the results, indicating that a linear relation exists between the buccal alcohol permeation rate and the plasma alcohol concentration. The same permeability coefficient, $4.8 \times 10^{-5}$ cm/sec, was shared by all of the tested individuals. In other words, 0.4 $\mu$g/min of alcohol permeates through the buccal mucosal on an average of 1.4 cm$^2$ for every 100 $\mu$g/ml (0.01%) of alcohol in the plasma.

Therefore, the results establish that the transbuccal permeation rate can be used to determine the actual plasma alcohol concentration of an individual.

The method of monitoring blood alcohol allowed a quantitative analysis of small changes in the amounts of alcohol in the patient's blood at any given time. The monitoring was quick and reliable.

EXAMPLE 4

Blood alcohol was monitored noninvasively in a laboratory subject according to the procedure of Example 1, except that the test subject was a dog. Additionally, ethanol was infused into the test subject at a rate of 3.6 g/hr. Also, the area of the cell's open bottom was 2.27 cm$^2$. The experimental results of Example 3 are shown graphically in FIG. 9.

Figure 9:
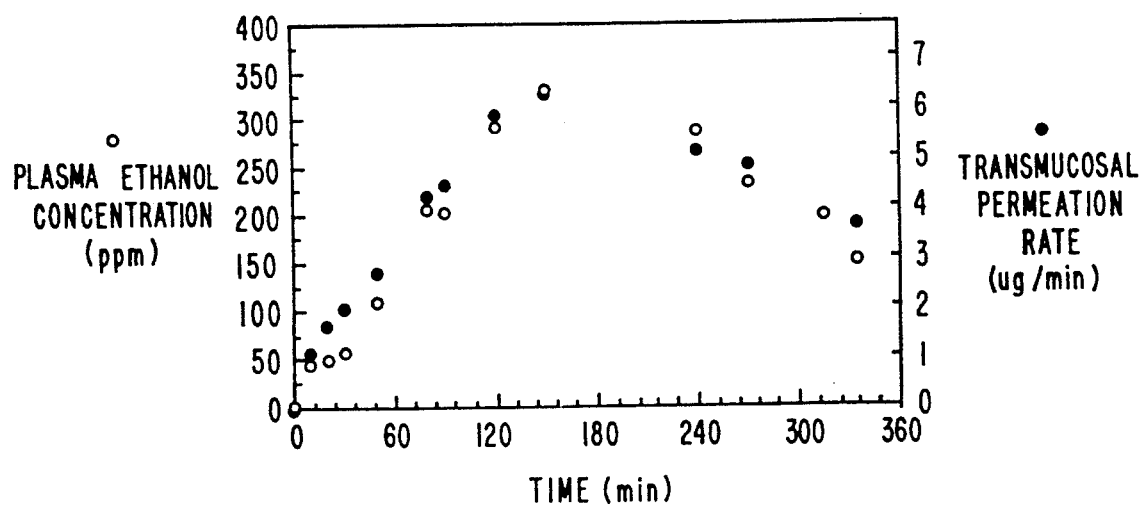
FIG. 9 is a graph of the alcohol concentration in plasma ($\mu g/ml$) versus buccal permeation rate ($\mu g/min$) for the results of Example 4.

An examination of FIG. 9 indicates that both the plasma ethanol concentration and the transmucosal permeation rate increased to a high point and then declined over a period of time after the ethanol infusion was stopped at t=195 minutes. The buccal permeation rate was proportional to the actual plasma concentration for the entire time course.

The results of this example demonstrate that the alcohol monitoring device may be employed to nonhuman subjects. Also, the results indicated the plasma ethanol concentration followed a straight line correlation to the transmucosal permeation rate. Therefore, the transmucosal permeation rate could be used to determine the actual plasma ethanol concentration of a dog.

EXAMPLE 5

Concentrations of alfentanil in plasma was monitored noninvasively in an anesthetized experimental dog through transbuccal mucosa alfentanil back permeation. Intravenous infusion of alfentanil was begun at 4.5

μg/kg/min at t=0 and terminated at t=80 min. A diffusion cell of 18 cm² was attached onto the dog's buccal mucosa. Starting at times of t=10, 30, 50, 70, 90, 120, 150, 180, 210, and 240 min., transbuccal alfentanil back permeation rates were measured (10 min per point) as follows: the cell and mucosa area in the cell was rinsed three times with water before 4 ml of receiving solution (water) was introduced into the cell. The receiving solution was kept in the cell for 10 min. before it was withdrawn for alfentanil concentration determinations. A blood sample was taken during the middle of each 10 min. period for plasma alfentanil concentration determinations. Alfentanil concentrations in both buccal receiving solutions and plasma were determined with a GC/MS method by a commercial lab.

Figure 10:
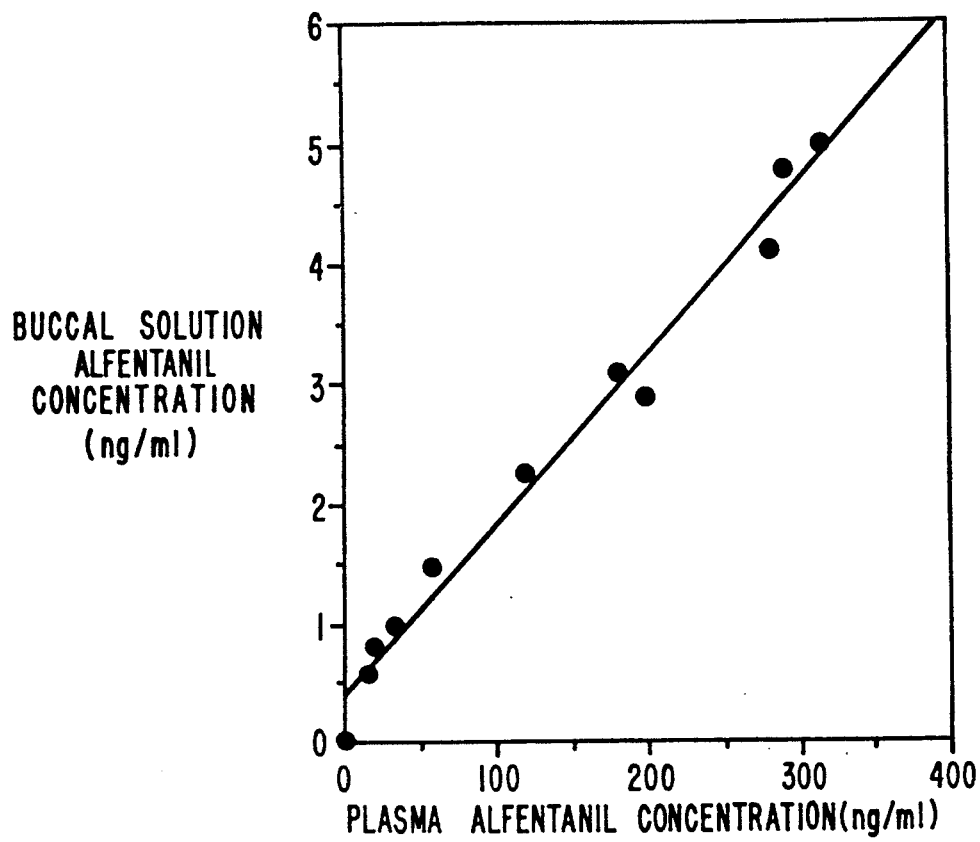
FIG. 10 is a graph of the alfentanil concentration in plasma ($ng/ml$) versus buccal permeation rate ($ng/ml$) for the results of Example 5.
Figure 11:
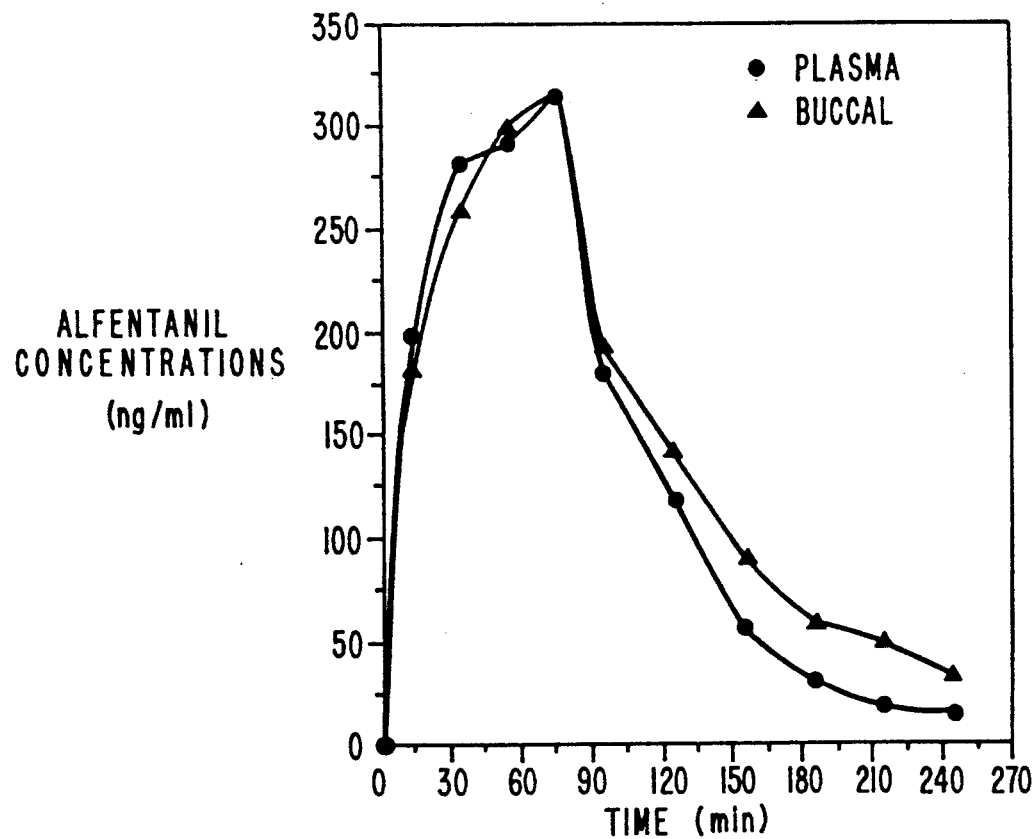
FIG. 11 is a graph of the two alfentanil concentrations illustrated in FIG. 10 which are plotted against time.

Alfentanil concentrations in buccal receiving solutions were plotted against plasma concentrations in FIG. 10. The two alfentanil concentrations were also plotted against time (on different scales) in FIG. 11.

Results shown in the figures indicate that there is a linear correlation between buccal alfentanil back permeation rate and actual plasma alfentanil concentrations. Therefore, the buccal permeation rate can be used to determine the actual plasma alfentanil concentrations.

EXAMPLE 6

Blood alcohol is monitored noninvasively in a laboratory subject according to the procedure of Example 1, except that a handle is attached to the diffusion cell. The results of the example indicate the plasma alcohol concentration of the tested individual follow a straight line correlation to the buccal permeation rate. Therefore, the buccal permeation rate can be used to determine the actual plasma alcohol concentration of an individual.

EXAMPLE 7

Blood alcohol is monitored noninvasively in a laboratory subject according to the procedure of Example 1, except that the diffusion cell is comprised of a hydrogel which is positioned against the buccal membrane. The results of the example indicate the plasma alcohol concentration of the tested individual follow a straight line correlation to the buccal permeation rate. Therefore, the buccal permeation rate can be used to determine the actual plasma alcohol concentration of an individual.

EXAMPLE 8

Blood alcohol is monitored noninvasively in a laboratory subject according to the procedure of Example 1, except that instead of water, the alcohol receiving medium includes cream. The results of the example indicate the plasma alcohol concentration of the tested individual follow a straight line correlation to the buccal permeation rate. Therefore, the buccal permeation rate can be used to determine the actual serum alcohol concentration of an individual.

EXAMPLE 9

Blood alcohol is monitored noninvasively in a laboratory subject according to the procedure of Example 1, except that the diffusion cell has a protective seal around it to create a contamination-free environment. The results of the example indicate the plasma alcohol concentration of the tested individual follow a straight line correlation to the buccal permeation rate. Therefore, the buccal permeation rate can be used to determine the actual plasma alcohol concentration of an individual.

EXAMPLE 10

Blood alcohol is monitored noninvasively in a laboratory subject according to the procedure of Example 1, except that the diffusion cell is comprised of polypropylene and held against the buccal membrane by flanges located about the periphery of the diffusion cell. The flanges receive an adhesive so that the diffusion cell may be maintained in position against the buccal membrane. The diffusion cell also has a handle for grasping. The alcohol receiving medium includes a surfactant.

The results of the example indicate the plasma alcohol concentration of the tested individual follow a straight line correlation to the buccal permeation rate. Therefore, the buccal permeation rate can be used to determine the actual plasma alcohol concentration of an individual.

In summary, the present invention permits noninvasive blood substance monitoring which can be performed nearly as rapidly as conventional monitoring techniques, but without the discomfort, inconvenience, and risks of current invasive techniques. The method of measuring blood alcohol is faster and more accurate than currently known methods of monitoring through dermal layers.

From the foregoing, it will be appreciated that the present invention provides apparatus and methods for noninvasive blood substance monitoring which avoids the inconvenience and risks associated with traditional invasive blood substance monitoring techniques.

Additionally the present invention provides apparatus and methods for noninvasive blood substance monitoring which provide reproducible and accurate correlation with actual blood substance levels.

The present invention also provides apparatus and methods for noninvasive blood substance monitoring which provide an environment free from contamination so that accurate results may be obtained.

Still yet the present invention also provides apparatus and methods for noninvasively monitoring the concentration of substance in the blood which are not limited to certain individuals, but instead can be applied to a wide variety of individuals.

Further, the present invention permits apparatus and methods for noninvasive blood substance monitoring which can be performed rapidly.

Finally, the present invention permits apparatus and methods for noninvasive blood substance monitoring which do not lead to inaccurate results due to contamination of the monitored sample by substances such as saliva.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for noninvasively collecting a desired substance from a subject comprising:

a) a substance receiving medium the substance receiving medium being capable of receiving the desired substance such that a quantity of the substance, which directly correlates with a subject's blood substance value, is capable of permeating the mucosal membrane into the substance receiving medium;

b) means for supporting the substance receiving medium against mucosal tissue of a subject from which the desired substance is to be collected; and c) means for isolating the substance receiving medium from contaminating sources, such that a quantity of the substance to be collected permeates into the substance receiving medium in a concentration approximately proportional to the concentration of such substance in the subject's blood.

2. An apparatus for noninvasively collecting a substance from a subject as recited in claim 1, wherein the apparatus further comprises means for temporarily positioning the substance receiving medium against the mucosal membrane such that substances may be collected from mucosal tissues.

3. An apparatus for noninvasively collecting a substance as defined in claim 2, wherein the temporarily positioning means comprises a handle attached to the housing to facilitate positioning of the apparatus against the mucosal membrane and removal of the apparatus.

4. An apparatus for noninvasively collecting a substance as defined in claim 1, wherein the means for supporting the substance receiving medium comprises a housing defining a receiving chamber therein and an opening to the receiving chamber.

5. An apparatus for noninvasively collecting a substance as defined in claim 1, wherein the means for isolating the substance receiving medium comprises a housing defining a receiving chamber therein and an opening to the receiving chamber.

6. An apparatus for noninvasively collecting a substance as defined in claim 1, further comprising a means for sealing the substance receiving medium from potential contaminants, the sealing means covering the substance receiving medium from the surrounding environment so as to prevent environmental contamination of the substance receiving medium.

7. An apparatus for noninvasively collecting a substance as defined in claim 6, wherein the sealing means comprises a seal constructed around the means for supporting the substance receiving medium against the mucosal membrane.

8. An apparatus for noninvasively collecting a substance as defined in claim 7, wherein the seal comprises polyethylene.

9. An apparatus for noninvasively collecting a substance as defined in claim 3, further comprising means for accessing the receiving chamber such that the substance receiving medium may be introduced into the receiving chamber or removed therefrom while the housing is positioned against the mucosal membrane.

10. An apparatus for noninvasively collecting a substance as defined in claim 1, further comprising a permeation enhancer capable of increasing the substance permeability across the mucosal membrane.

11. An apparatus for noninvasively collecting a substance as defined in claim 1, wherein the substance receiving medium comprises water.

12. An apparatus for noninvasively collecting a desired substance from a subject as in claim 1, further comprising means for joining the substance receiving medium to the mucosal tissue such that communication is established and the desired substance may travel therebetween.

13. An apparatus for noninvasively collecting a substance as defined in claim 12, wherein the means for joining the substance receiving medium to the mucosal membrane comprises a hydrogel.

14. An apparatus for noninvasively collecting a substance as defined in claim 12, wherein the means for joining the substance receiving medium to the mucosal membrane comprises a cream.

15. An apparatus for noninvasively collecting a substance as defined in claim 12, wherein the means for joining the substance receiving medium to the mucosal membrane comprises a suspension.

16. An apparatus for noninvasively collecting a substance as defined in claim 12, wherein the means for joining the substance receiving medium to the mucosal membrane comprises an emulsion.

17. An apparatus for noninvasively collecting a substance as defined in claim 12, wherein the means for joining the substance receiving medium to the mucosal membrane comprises a semisolid composition.

18. An apparatus for noninvasively collecting a substance as defined in claim 1, further comprising means for regulating the substance permeation rate in order to provide a calibrated permeation rate despite variations in substance permeation from individual to individual and from time to time.

19. An apparatus for noninvasively collecting a substance as defined in claim 18, wherein the regulating means further comprises at least one rate-regulating membrane placed between the mucosal membrane and the substance receiving medium to regulate the quantity of the desired substance entering the substance receiving medium.

20. An apparatus for noninvasively collecting a substance as in claim 1, wherein the apparatus further comprises means for filtering the fluids traveling from the mucosal membrane to the substance receiving medium.

21. An apparatus for noninvasively collecting a substance as in claim 20, wherein the filtering means comprises a semipermeable membrane for purifying the substance that travels from the mucosal membrane to the substance receiving medium.

22. An apparatus for noninvasively collecting a substance as recited in claim 1, wherein the apparatus further comprises means for continually measuring the substance receiving medium such that removal of the device from the mucosal membrane and contamination of the substance receiving medium is avoided.

23. An apparatus for noninvasively collecting a substance as recited in claim 22, wherein the continual measurement means comprises an elongate tube communicating with the substance receiving medium.

24. An apparatus for noninvasively collecting a substance as in claim 1, wherein the desired substance is alcohol.

25. An apparatus for noninvasively collecting a substance as in claim 1, wherein the desired substance is an intravenous anesthetic.

26. An apparatus for noninvasively collecting a substance as in claim 1, wherein the desired substance is a narcotic.

27. An apparatus for noninvasively collecting a substance as in claim 1, wherein the desired substance is a blood electrolyte.

28. An apparatus for noninvasively collecting a substance as in claim 1, wherein the desired substance is a bronchodilator drug.

29. An apparatus for noninvasively collecting a substance as in claim 1, wherein the desired substance is a cardiac drug.

30. An apparatus for noninvasively collecting a substance as in claim 1, wherein the desired substance is a psychic acting drug.

31. An apparatus for noninvasively collecting a substance as in claim 1, wherein the desired substance is an endogenous peptide.

32. An apparatus for noninvasively collecting a substance from a subject comprising:
- a housing, the housing being adapted for placement against a subject's mucosal tissue, the housing including a chamber which is in communication with the mucosal tissue when the housing is placed against the tissue while being isolated from contamination from sources other than the mucosal tissue; and
- a substance receiving medium contained within the chamber, the medium capable of accepting the desired substance.

33. An apparatus for noninvasively collecting a substance as defined in claim 32, wherein the substance receiving medium comprises water.

34. An apparatus for noninvasively collecting a substance as defined in claim 32, wherein the apparatus further comprises a hydrogel as the substance receiving medium.

35. An apparatus for noninvasively collecting a substance as defined in claim 32, wherein the apparatus further comprises a semisolid composition as the substance receiving medium.

36. An apparatus for noninvasively collecting a substance as defined in claim 32, wherein the apparatus further comprises a composition capable of reacting with a substance to form a substantially insoluble product, in proportion to the concentration substance.

37. An apparatus for noninvasively collecting a substance as defined in claim 32, wherein the substance receiving medium further comprises a permeation enhancer capable of increasing the substance permeability across the mucosal membrane.

38. An apparatus for noninvasively collecting a substance as defined in claim 32, further comprising means for regulating the substance permeation rate in order to provide a calibrated permeation rate despite variations in substance permeation from individual to individual and from time to time.

39. An apparatus for noninvasively collecting a substance as defined in claim 32, further comprising means for accessing the receiving chamber such that substance receiving medium may be introduced into the receiving chamber or removed therefrom while housing is positioned against the mucosal membrane.

40. An apparatus for noninvasively collecting a substance as in claim 32, wherein the apparatus further comprises means for filtering the fluids traveling from the mucosal membrane to the substance receiving medium.

41. An apparatus for noninvasively collecting substance as in claim 40, wherein the filtering means comprises a semipermeable membrane for purifying the substance that travels from the mucosal membrane to the substance receiving medium.

42. An apparatus for noninvasively collecting a substance as in claim 32, wherein the apparatus further comprises means for continually measuring the substance receiving medium such that removal of the device from the mucosal membrane and contamination of the substance receiving medium is avoided.

43. An apparatus for noninvasively collecting a substance as recited in claim 42, wherein the continual measurement means comprises an elongate tube communicating with the substance receiving medium.

44. An apparatus for noninvasively collecting a substance as in claim 32, wherein the monitored substance is alcohol.

45. An apparatus for noninvasively collecting a substance as in claim 32, wherein the monitored substance is an intravenous anesthetic.

46. An apparatus for noninvasively collecting a substance as in claim 32, wherein the monitored substance is a narcotic.

47. An apparatus for noninvasively collecting a substance as in claim 32, wherein the monitored substance is a blood electrolyte.

48. An apparatus for noninvasively collecting a substance as in claim 32, wherein the monitored substance is a bronchodilator drug.

49. An apparatus for noninvasively collecting a substance as in claim 32, wherein the monitored substance is a cardiac drug.

50. An apparatus for noninvasively collecting a substance as in claim 32, wherein the monitored substance is a psychic acting drug.

51. An apparatus for noninvasively collecting a substance as in claim 32, wherein the monitored substance is an endogenous peptide or other hormone.

52. An apparatus for noninvasively collecting a desired substance from a subject comprising:
- a housing, the housing being adapted for placement against a subject's mucosal tissue, the housing including a chamber wherein the desired substance is collected from the mucosal tissue when the housing is placed against the tissue, the chamber being isolated from contamination from sources other than the mucosal tissue; and
- at least one rate regulating membrane placed between the mucosal membrane and the chamber to achieve a rate regulating function with regard to the quantity of the desired substance entering the chamber, the chamber receiving the desired substance such that a quantity of a substance, which directly correlates on a real time basis with a subject's blood substance concentration, is capable of permeating the mucosal membrane and the rate regulating membrane into the chamber.

53. An apparatus for noninvasively collecting a substance as defined in claim 52, wherein the apparatus further comprises a substance receiving medium contained within the chamber, the medium capable of accepting the desired substance.

54. An apparatus for noninvasively collecting a substance from a subject as in claim 52, wherein the apparatus further comprises means for temporarily positioning the housing against the mucosal membrane such that substances may be collected from mucosal tissues.

55. An apparatus for noninvasively collecting a substance from a subject as in claim 52, wherein the temporarily positioning means is a handle attached to the housing to facilitate positioning of the apparatus against the mucosal membrane and removal of the apparatus.

56. An apparatus for noninvasively collecting a substance as defined in claim 32, wherein the apparatus further comprises a composition capable of reacting with a substance to produce a color change.

57. An apparatus for noninvasively collecting a substance as defined in claim 32, wherein the apparatus further comprises a composition capable of reacting with a substance to produce an electric current.

58. An apparatus for noninvasively collecting a substance as defined in claim 31, wherein the apparatus further comprises a composition capable of reacting with a substance to produce a hormone.

* * * * *

UNITED STATES PATENT AND TRADEMARK OFFICE
CERTIFICATE OF CORRECTION

PATENT NO. : 5,291,887
DATED : March 8, 1994
INVENTOR(S) : THEODORE H. STANLEY et al.

It is certified that error appears in the above-indentified patent and that said Letters Patent is hereby corrected as shown below:

Abstract, Title page, column 2, line 9, "an" should be --a--
Column 12, line 58, "pallete" should be --palate--
Column 18, line 48, "a alcohol" should be --an alcohol--
Column 19, line 42, "an caucasian" should be --a Caucasian--
Column 19, line 65, "an caucasian" should be --a Caucasian--

Signed and Sealed this

Twenty-seventh Day of September, 1994

Attest:

BRUCE LEHMAN

Attesting Officer        Commissioner of Patents and Trademarks